(12) United States Patent
Bitfu et al.

(10) Patent No.: US 6,384,052 B1
(45) Date of Patent: May 7, 2002

(54) ANTICOCCIDIAL COMPOUNDS

(75) Inventors: Tesfaye Bitfu, Westfield; Danqing D. Feng, Branchburg Township, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/709,959

(22) Filed: Nov. 10, 2000

Related U.S. Application Data
(60) Provisional application No. 60/165,142, filed on Nov. 12, 1999.

(51) Int. Cl.$^7$ ............... A61K 31/445; A61K 43/40; C07D 211/56; C07D 207/00
(52) U.S. Cl. ............ 514/318; 514/326; 514/327; 514/330; 514/333; 514/347; 514/362; 514/354; 514/427; 546/184; 546/193; 546/208; 546/216; 546/223; 546/244; 546/248; 548/518; 548/530; 548/544; 548/564
(58) Field of Search ................ 514/318, 326, 514/327, 330, 333, 347, 362, 354, 427; 546/184, 193, 208, 216, 223, 244, 248; 548/518, 530, 541, 564

(56) References Cited

U.S. PATENT DOCUMENTS
5,792,778 A * 8/1998 de Laszlo et al. .......... 514/318

FOREIGN PATENT DOCUMENTS
| WO | WO 97/16426 | 5/1997 |
| WO | WO 97/48725 | 12/1997 |

OTHER PUBLICATIONS

Chemical Abstract vol. 126 No. 225212, DeLaszlo et al, "Preparation of arylpyrroles as cytokine inhibitors" (1997).*

Lowenthal, et al., Database Medline on Stn, No. 97474409, Abstract, J. Interferon and Cytokine Res., vol. 17 (9), pp. 551–558, 1997.

* cited by examiner

*Primary Examiner*—Alan L. Rotman
*Assistant Examiner*—Raymond Covington
(74) *Attorney, Agent, or Firm*—Mollie M. Yang; David L. Rose

(57) ABSTRACT

Trisubstituted pyrroles are useful in the control of coccidiosis in poultry.

15 Claims, No Drawings

ANTICOCCIDIAL COMPOUNDS

CROSS-REFERENCE TO RELATED APPLICATIONS

This application is a non-provisional application related to U.S. Provisional Application Serial No. 60/165,142 filed on Nov. 12, 1999 priority of which is claimed hereunder.

SUMMARY OF THE INVENTION

The present invention provides trisubstituted pyrroles as anticoccidial agents, their use in controlling coccidiosis, and compositions containing them.

BACKGROUND OF THE INVENTION

Coccidiosis is a widespread poultry disease which causes severe pathology in the intestines and ceca of poultry. It is produced by infections with protozoans of the genus Eimeria; some of the most significant of these species are *E. tenella, E. acervulina, E. mitis, E. necatrix, E. brunetti*, and, *E. maxima*. This disease is generally spread by the birds picking up the organism at its infectious stage in droppings on contaminated litter or ground, or by way of food or drinking water. The disease is manifested by hemorrhage, accumulation of blood in the ceca, passage of blood in the droppings, weakness and digestive disturbances. The disease often terminates in the death of the animal, but the fowl which survive severe infections have had their market value substantially reduced as a result of the infection. Coccidiosis is, therefore, a disease of great economic importance and extensive work has been done to find new and improved methods for controlling and treating coccidial infections in poultry.

In the poultry industry it is common practice to include anticoccidial agents in poultry feed for most of the bird's life to control or prevent coccidiosis outbreak. However, there is a risk that the causative organisms will develop resistance after continuous or repeated exposure to any particular drug. Furthermore, conventionally used anticoccidial agents such as sulfanilamides, nitrofurans, quinolines, antithiamines, benzoamides, and polyether-based antibiotics are often toxic to the hosts. Therefore, there is a continuing need to identify new anticoccidial compounds, preferably in a different chemical class from agents currently in use.

U.S. Pat. No. 5,792,778 discloses 2-substituted aryl pyrroles as useful for the treatment of diseases related to excessive cytokine production in mammals. The compound 2-(4-fluorophenyl)-5-(N-methylpiperidin-4-yl)-3-(4-pyridyl)pyrrole is specifically disclosed therein.

DETAILED DESCRIPTION OF THE INVENTION

The present invention provides compounds of formula (I) or a physiologically acceptable salt thereof:

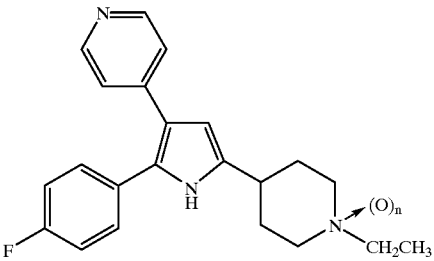

wherein n is 0 or 1.

Compounds of formula (I) are useful in the prevention and treatment of protozoal diseases in animals. In particular, the compounds are useful in the prevention and treatment of coccidiosis in poultry.

Compounds of the present invention may be prepared by methods generally disclosed in U.S. Pat. No. 5,792,778, and the following procedures represent non-limiting examples thereof.

2-(4-Fluorophenyl)-5-(N-ethylpiperidin-4-yl)-3-(4-pyridyl)pyrrole and its dihydrochloride salt To a suspension of 2-(4-fluorophenyl)-5-(piperidin-4-yl)-3-(4-pyridyl)-pyrrole (U.S. Pat. No. 5,792,77, 1000 mg, 3.11 mmol; hereinafter referred to as Compound A) and acetic acid (0.18 ml, 3.11 mmol) in anhydrous 1,2-dichloroethane (50 ml) under nitrogen at room temperature, acetaldehyde (0.21 ml, 3.73 mmol) and sodium triacetoxyborohydride (989 mg, 4.67 mmol) were added slowly. The resulting mixture was allowed to stir for 2 hours. The crude product was purified by flash silica gel column (MeOH-CH$_2$Cl$_2$, 8:92 v/v containing 1% NH$_4$OH). After drying, 930 mg of 2-(4-fluorophenyl)-5-(N-ethylpiperidin-4-yl)-3-(4-pyridyl) pyrrole (Compound B) was obtained as the free base.

NMR (CD$_3$OD) σ8.25(d, J=6.23 Hz, 2H), 7.34(m, 2H), 7.25(d, J=6.27 Hz, 2H), 7.09(m, 2H), 6.19(s, 1H), 3.07(d, J=11.94 Hz, 2H), 2.65(m, 1H), 2.48(qt, J=7.33 Hz, 2H), 2.11(t, J=9.95 Hz, 2H), 2.02(d, J=11.21 Hz, 2H), 1.79(m, 2H), 1.14(t, J=7.24 Hz, 3H); MS(ESI)=350.3.

An alternative procedure to prepare compound B from compound A is as follows: Compound A (1.0 g) in 25 ml dry methylene chloride and 10 ml of 2.5 N NaOH was cooled to 0° C. and treated with 0.25 ml of acetyl chloride dropwise. After 2 hours the solution was allowed to warm up to room temperature and stirring was continued overnight. The solution was treated with distilled water and extracted with methylene chloride. The methylene chloride layer was separated, dried over anhydrous sodium sulfate, filtered and evapotated to give 1.33 g of crude amide reaction product, which was purified by flash column (silica, methylene chloride:methanol:25% NH4OH 90:9:1) to yield 0.7 g of 2-(4-fluorophenyl)-5-(N-acetylpiperidin-4-yl)-3-(4-pyridyl) pyrrole. This amide was dissolved in 15 ml of tetrahydrofuran and treated with 3 ml of 1M lithium aluminum hydride (LAH) in THF under an atmosphere of nitrogen at room temperature. After completion of addition of LAH, the solution was refluxed for two hours, cooled to 0° C., quenched with water (0.19 ml) and 2.5 N NaOH (0.19 ml) and filtered. The filtrate was dried over sodium sulfate, filtered, evaporated and purified by flash column as shown above to give compound B (0.65 g).

Compound B (349 mg) was suspended in 10 ml of methanol and treated with 2 ml of 1M HCl in methanol. After stirring the resulting yellow solution under nitrogen for 10 minutes, solvent was evaporated and product was kept under vacuum overnight to yield 420 mg of dihydrochloride salt of compound B.

2-(4-Fluorophenyl)-5-(N-ethylpiperidin-4-yl)-3-(4-pyridyl) pyrrole, N-oxide

To a suspension of Compound B (700 mg, 2.0 mmol) in anhydrous dichloromethane (50 ml) under nitrogen at 0° C., was added 3-chloroperoxybenzoic acid (666 mg, 2.2 mmol) slowly. The resulting solution was allowed to stir for 2 hours at 0° C. and for 0.5 hour at room temperature. To the resulting clear solution potassium carbonate (415 mg, 3.0 mmol) was added, and the reaction mixture was stirred for 0.75 hour. The white precipitate was removed by filtration. The crude product was purified by flash silica gel chromatography (MeOH-CH$_2$Cl$_2$, 10:90 v/v containing 1% NH$_4$OH). After drying, 505 mg of 2-(4-fluorophenyl)-5-(N-ethylpiperidin-4-yl)-3-(4-pyridyl)pyrrole N-oxide was obtained. NMR (CD$_3$OD)σ8.26(d, J=6.27 Hz, 2H), 7.35(m, 2H), 7.26(d, J=6.13 Hz, 2H), 7.11(m, 2H), 6.28(s, 1H), 3.35(m, 6H), 2.85(m, 1H), 2.46(m, 2H), 2.00(m, 2H), 1.39(t, J=7.10 Hz, 3H); MS(ESI)=366.3

Compound of the present invention is basic and therefore can form salts with organic or inorganic acids. Salts are prepared from inorganic or organic acids that are physiologically acceptable to the recipient hosts including, but are not limited to, acetic, benzenesulfonic, benzoic, camphorsulfonic, citric, ethanesulfonic, fumaric, gluconic, glutamic, hydrobromic, hydrochloric, lactic, maleic, malic, mandelic, methanesulfonic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids. The term "physiologically acceptable" means generally safe and tolerated by the host species to be treated.

It will be understood that, as used herein, references to the compound of the present invention are meant to also include its N-oxide and salts. The term "composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a physiologically acceptable carrier.

Compound of the present invention can be employed for the control of coccidiosis in any species. The term "control of coccidiosis" includes prophylactic use to prevent coccidiosis as well as use to treat coccidiosis after infection has occurred. Chickens and turkeys are the species most commonly in need for control of coccidiosis, but compound of the present invention can also be used with other poultry species, such as ducks, geese, quail, pheasants, emus and ostriches, as well as with species other than poultry, such as cattle, sheep, swine, and the like. Compound of the present invention can be used to prevent or treat coccidiosis caused by any species of the causative protozoa including *Eimeria acervulina, Eimeria brunetti, Eimeria maxima, Eimeria mitis, Eimeria necatrix, Eimeria tenella, Eimeria meleagrimitis, Eimeria gallopavonis, Eimeria adenoeides, Eimeria dispersa* and other protozoas.

The compound of the present invention may be used in the usual fashion of anticoccidials, that is, because coccidiosis is a malady of the intestinal tract, an anticoccidial must be administered in a way to reach the intestinal tract. This is typically achieved by incorporating the anticoccidial agent in the feed. Anticoccidials are sometimes administered via the drinking water, and this route is also possible for the present compound. In the most preferred practice, however, the present compound is administered in the feed.

The compound of the present invention may be formulated into preventive/curative medicament for poultry against coccidiosis in accordance with any conventional methods well known in the field of art. Thus, the compound of the present invention can be formulated into spreads, granules, suspensions, solutions, premixes, capsules, emulsions concentrates, tablets, feedstuff and so forth, using the compound either as a single substance or with or without suitable carrier that are ordinarily used for this kind of medicaments, and using, at times, an excipient, a disintegrating agent, a sliding agent, a coating agent, and so forth. The carriers usable in the preparations according to the present invention are not limited so long as they can be added to the livestock feed or drinking water of poultry, and examples include water, milk sugar, cane sugar, talc, colloidal silica, pectin, wheat flour, rice bran, corn flour, soybean, oil cake, ground or powdered grain, and other commercial livestock feeds for poultry. Although there are no specific limitations to the content or concentration of the active component the preferable content is 0.1 to 99% by weight, more preferably, 0.1 to 50% by weight.

Of the various methods of administering the anticoccidials of this invention to poultry, they are most conveniently administered as a component of a feed composition. The novel anticoccidial may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal and calcium carbonate and vitamins.

When the compound according to the present invention is used as an additive to the feed, it is typically incorporated into a "premix." The premix contains the active agent or agents as well as physiologically acceptable carriers and feedstuffs. The premix is relatively concentrated and is adapted to be diluted with other carriers, vitamin and mineral supplements, and feedstuffs to form the final animal feed. Premixes which are intermediate in concentration of active agent between a first premix and the final animal feed are sometimes employed in the industry and can be used in implementing the present invention. When employing the present compound as sole active agent, a premix desirably contains the agent at a concentration of from 0.1 to 50.0% by weight. Preferred premixes will generally contain the present compound at a concentration of from 0.5 to 25.0%, by weight. The identity of the other components of the premix and ultimate animal feed is not critical. In final feeds, the concentration of the active agent is not critical and will depend on various factors known to those skilled in the art. Such factors include the relative potency of the particular active agent and the severity of the coccidial challenge. In general, a final feed employing compound of the present invention as the sole anticoccidial will contain from about 0.002 to about 0.02% by weight of said compound, preferably from about 0.002 to about 0.01%.

The present invention contemplates using a compound of formula (I) as sole anticoccidial agent as well as in combination with one or more other anticoccidial agents. Suitable anticoccidials for combination use include, but are not limited to, amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril. When used in combination with one or more other anticoccidial agent, the compound of formula (I) may be administered at or lower than the effective doses when used alone; for example, the final feed may contain about 0.0001 to about 0.02% by weight, or preferably from about 0.0005 to about 0.005% of a compound of formula (I). Similarly, the second anticoccidial agent in the combination may be used in an amount at or lower than those commonly used as a sole anticoccidial. The combination may be formulated into medicament for poultry use as described previously.

The formulated medicament may contain, in addition to anticoccidial agent(s) other therapeutic or nutritional agents commonly administered to poultry in the feed or drinking water; such other agents may be, for example, parasiticides, antibacterials, and growth promoters.

Compound of the present invention and 2-(4-fluorophenyl)-5-(N-methylpiperidin-4-yl)-3-(4-pyridyl)pyrrole were evaluated in anticoccidiosis assay and toxicology studies. In these studies, medicated diets were prepared by dissolving the proper quantity of the test compound in dimethylsulfoxide or acetone, mixing the resultant solution into a few grams of the basal diet, and then placing the mixture under a fume hood for dehydration. The dry mixture is made into a uniform premix with an electric grinder, and then blended with the desired quantity of basal diet for the final formulation in a commercial bowl mixer.

Anticoccidiosis Assay

One-day-old White Leghorn chickens are obtained from a commercial hatchery and acclimated in a holding room. At three days of age the test animals are selected by weight, wingbanded, and randomly placed on medicated or control diets for the duration of the experiment. One or two replicates of two birds are utilized per treatment. Following 24 h premedication, in each replicate one bird is infected with *Eimeria acervulina*, the other bird is infected with *E. tenella*. Both strains of Eimeria are sensitive to all anticoccidial products, and have been maintained in laboratory conditions for over 25 years. The inocula consist of sporulated oocysts in tap water suspensions, administered at a dose rate of 0.25 ml per bird. The inocula levels are selected by previous dose titrations to provide a low to moderate level of infection. The *E. acervulina* portion of the experiment is terminated on Day 5, the *E. tenella* on Day 6 post infection. The measured parameters are weight gain, feed consumption and oocyst production. *E. tenella* lesion scores are also recorded for background information. Treatments which provide at least 80% reduction in oocyst production are considered active, those with 50–79% are considered partially active, and those with <50% are considered inactive. The same numerical categories in weight gain and feed consumption differentiate among treatments with good, fair or poor productivity.

In this assay both 2-(4-fluorophenyl)-5-(N-ethylpiperidin-4-yl)-3-(4-pyridyl)pyrrole and 2-(4-fluorophenyl)-5-(N-methylpiperidin-4-yl)-3-(4-pyridyl)-pyrrole are active at 100 ppm, and partially active at 50 and 75 ppm.

Toxicity Evaluation

Day-old male broiler chickens are received on Day 0 of the trial, weighed, wingbanded, and placed on medicated or control diet in standard battery cages. Three treatments are used in the study: (A) medicated diet containing 125 ppm of 2-(4-fluorophenyl)-5-(N-methylpiperidin-4-yl)-3-(4-pyridyl)pyrrole; (B) medicated diet containing 125 ppm of 2-(4-fluorophenyl)-5-(N-ethylpiperidin-4-yl)-3-(4-pyridyl) pyrrole; and (C) no medication. A total of 48 chickens are utilized per treatment. Of these, 12 birds (2 replicates of 6) are examined on D7, D14, D24 and D38 for liver necrosis and urate crystal deposition. Growth rates, feed efficiency and plasma levels are determined for background information. The trial is terminated on D38.

None of the chickens in the (B) treatment group showed liver necrosis or urate crystal deposition. In the (A) treatment group, 3/12 and 4/12 chickens examined on D14 and D38, respectively, had urate crystal deposition in the kidneys.

Acute Toxicity Evaluation

For acute toxicity evaluation, chickens are dosed intraperitoneally twice a day at desired dose for three days. On day 4 birds are necropsied and examined for gross lesions and weight suppression. Two chickens are used in each treatment group. In the acute toxicity model, none of the chickens treated with the N-ethyl compound showed liver necrosis when dosed at 100 mg/kg/day. However, birds dosed at 100 mg/kg/day with the N-methyl analog demonstrated gross liver lesions.

Results of the efficacy and toxicity evaluations show that even though both N-methyl and N-ethyl compounds show activity in the anticoccidiosis assay, unexpectedly, the N-ethyl compound does not have the renal and liver liabilities in chickens observed with the N-methyl compound.

What is claimed is:

1. A compound having the formula (I), or a physiologically acceptable salt thereof

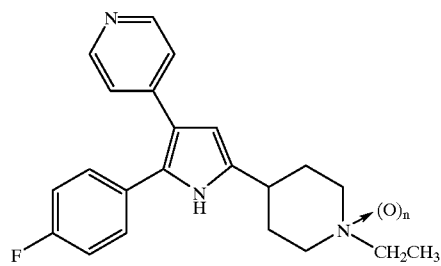

(I)

wherein n is 0 or 1.

2. A method for controlling coccidiosis in poultry which comprises administering to said poultry an anticoccidially effective amount of the compound of claim 1.

3. A method for controlling coccidiosis in poultry which comprises administering to said poultry a therapeutically effective amount of a combination of anticoccidial agents comprising a compound of claim 1 and a second anticoccidial agent.

4. A method of claim 3 wherein said second anticoccidial agent is selected from the group consisting of amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril.

5. A method of claim 4 wherein said second anticoccidial agent is selected from the group consisting of amprolium, ethopabate, lasalocid, monensin, salinomycin, and diclazuril.

6. A composition for controlling coccidiosis which comprises a compound of claim 1 and a physiologically acceptable carrier.

7. A composition of claim 6 wherein said carrier is poultry feedstuff.

8. A composition of claim 6 wherein said carrier is poultry feed premix.

9. A composition of claim 6 further comprising a second anticoccidial agent.

10. A composition of claim 9 wherein said second anticoccidial agent is selected from the group consisting of amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril.

11. A composition of claim 10 wherein said second anticoccidial agent is selected from the group consisting of amprolium, ethopabate, lasalocid, monensin, salinomycin, and diclazuril.

12. A composition of claim 7 wherein said second anticoccidial agent is selected from the group consisting of amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril.

13. A composition of claim 12 wherein said second anticoccidial agent is selected from the group consisting of amprolium, ethopabate, lasalocid, monensin, salinomycin, and diclazuril.

14. A composition of claim 8 wherein said second anticoccidial agent is selected from the group consisting of amprolium, ethopabate, clopidol, meticlorpindol, decoquinate, dinitolmide, halofuginone, lasalocid, maduramicin, monensin, narasin, nicarbazin, chlortetracycline, oxytetracycline, robenidine, salinomycin, semduramicin, and diclazuril.

15. A composition of claim 14 wherein said second anticoccidial agent is selected from the group consisting of amprolium, ethopabate, lasalocid, monensin, salinomycin, and diclazuril.

* * * * *